(12) United States Patent
Rapoport

(10) Patent No.: US 9,061,112 B2
(45) Date of Patent: Jun. 23, 2015

(54) CHAMBER FOR HOUSING ANIMALS DURING ANAESTHETIC PROCEDURES

(75) Inventor: Uri Rapoport, Shoham (IL)

(73) Assignee: ASPECT IMAGING LTD, Shoham (IL)

(*) Notice: Subject to any disclaimer, the term of this patent is extended or adjusted under 35 U.S.C. 154(b) by 0 days.

(21) Appl. No.: 13/059,064

(22) PCT Filed: Sep. 10, 2009

(86) PCT No.: PCT/IL2009/000884
§ 371 (c)(1),
(2), (4) Date: Mar. 7, 2011

(87) PCT Pub. No.: WO2010/029547
PCT Pub. Date: Mar. 18, 2010

(65) Prior Publication Data
US 2011/0162652 A1    Jul. 7, 2011

Related U.S. Application Data

(60) Provisional application No. 61/095,642, filed on Sep. 10, 2008, provisional application No. 61/095,958, filed on Sep. 11, 2008, provisional application No. 61/121,558, filed on Dec. 11, 2008.

(51) Int. Cl.
*A61M 16/01* (2006.01)
*A61D 7/04* (2006.01)
*A01K 1/03* (2006.01)

(52) U.S. Cl.
CPC ............. *A61M 16/01* (2013.01); *A01K 1/03* (2013.01); *A61D 7/04* (2013.01); *A61M 2250/00* (2013.01)

(58) Field of Classification Search
CPC .... A61M 16/104; A61M 16/01; A62B 13/00; A62B 31/00; A01K 1/00; A01K 1/03; A01K 1/031; A01K 1/035; A01K 1/0356; A01K 1/0047; A01K 41/00; A61D 7/04
USPC .......................... 128/202.12, 203.12, 205.26; 119/417–420; 600/21, 22, 208; 49/367
See application file for complete search history.

(56) References Cited

U.S. PATENT DOCUMENTS 2,436,291 A    2/1948  Daniel et al.
2,528,332 A   10/1950  Berquist et al.
(Continued)

FOREIGN PATENT DOCUMENTS

DE  21 2009 000 105 U1  7/2011
WO       01/60076 A1    8/2001

OTHER PUBLICATIONS

International Search Report dated Apr. 6, 2010 in corresponding application PCT/IL2009/000884.
Office Action issued by the Israeli Patent Office dated Jan. 20, 2014 in corresponding Israeli Application No. 211219.
Aspect Imaging Ltd., "Shutting Assembly for Closing an Entrance of an MRI Device", co-pending U.S. Appl. No. 14/540,163, filed Nov. 13, 2014.
Aspect Imaging Ltd, "MRI—Incubator's Closure Assembly", co-pending U.S. Appl. No. 14/539,442, filed Nov. 12, 2014.
(Continued)

*Primary Examiner* — Valerie L Skorupa
(74) *Attorney, Agent, or Firm* — The Law Offices of Michael Kondoudis

(57) ABSTRACT

The present invention provides a chamber having at least one operator hand access port; the port comprising a port aperture located within the chamber wall; and at least two flexible non-resilient lightweight sealing gas-tight flaps (SFs), disposed the same plane of the port aperture in an overlapping manner, entirely enclosing the port aperture; each of the SFs is defined by a port aperture edge and chamber edges; the chamber edges are anchored to the chamber wall along more than half of the perimeter of the flap, at a distance from the center of the port greater than the radius of the port and beyond its perimeter; the port aperture edge of each flap is stretched across an entire chord of the port aperture; stretched port apertures edges define an interior access zone, disposed the same plane of the port aperture, characterized solely by the port aperture edges.

12 Claims, 12 Drawing Sheets

(56) References Cited

U.S. PATENT DOCUMENTS

| | | | |
|---|---|---|---|
| 2,803,370 | A | 8/1957 | Lennard |
| 3,086,674 | A | 4/1963 | Scheuerman |
| 3,450,450 | A | 6/1969 | Hopkins et al. |
| 4,251,123 | A | 2/1981 | Brackenbush et al. |
| 4,328,904 | A * | 5/1982 | Iverson ............ 220/229 |
| 4,331,254 | A | 5/1982 | Haggerty |
| 4,348,985 | A * | 9/1982 | Leong ............ 119/420 |
| 5,012,763 | A * | 5/1991 | Morrison ............ 119/302 |
| 5,038,515 | A * | 8/1991 | Moorhead ............ 43/55 |
| 5,104,206 | A | 4/1992 | Carlson et al. |
| 5,194,041 | A * | 3/1993 | Trexler ............ 454/251 |
| 5,331,920 | A * | 7/1994 | Coiro et al. ............ 119/418 |
| 5,976,871 | A * | 11/1999 | Walker et al. ............ 435/307.1 |
| 6,352,076 | B1 | 3/2002 | French |
| 6,981,966 | B2 | 1/2006 | Green et al. |
| 7,037,254 | B2 | 5/2006 | O'Connor et al. |
| 7,113,217 | B2 | 9/2006 | Nilson et al. |
| 7,222,587 | B2 * | 5/2007 | Hagel ............ 119/482 |
| 7,789,820 | B2 * | 9/2010 | Akers et al. ............ 600/21 |
| 8,851,018 | B2 | 10/2014 | Rapoport et al. |
| 8,896,310 | B2 | 11/2014 | Rapoport |
| 2004/0216737 | A1* | 11/2004 | Anderson et al. ......... 128/203.12 |
| 2006/0161050 | A1* | 7/2006 | Butler et al. ............ 600/208 |
| 2007/0238946 | A1* | 10/2007 | Chiodo ............ 600/407 |
| 2011/0162652 | A1 | 3/2011 | Rapoport |
| 2011/0186049 | A1 | 3/2011 | Rapoport |
| 2011/0234347 | A1 | 9/2011 | Rapoport |
| 2011/0304333 | A1 | 12/2011 | Rapoport |
| 2012/0071745 | A1 | 3/2012 | Rapoport |
| 2012/0073511 | A1 | 3/2012 | Rapoport et al. |
| 2012/0077707 | A1 | 3/2012 | Rapoport |
| 2012/0119742 | A1 | 5/2012 | Rapoport |
| 2013/0079624 | A1 | 3/2013 | Rapoport |
| 2013/0109956 | A1 | 5/2013 | Rapoport |
| 2013/0237803 | A1 | 9/2013 | Rapoport |
| 2013/0328559 | A1 | 12/2013 | Rapoport |
| 2013/0328560 | A1 | 12/2013 | Rapoport |
| 2013/0328563 | A1 | 12/2013 | Rapoport |
| 2014/0050827 | A1 | 2/2014 | Rapoport |
| 2014/0051973 | A1 | 2/2014 | Rapoport et al. |
| 2014/0051974 | A1 | 2/2014 | Rapoport et al. |
| 2014/0051976 | A1 | 2/2014 | Rapoport et al. |
| 2014/0099010 | A1 | 4/2014 | Rapoport |
| 2014/0103927 | A1 | 4/2014 | Rapoport |
| 2014/0117989 | A1 | 5/2014 | Rapoport |
| 2014/0128725 | A1 | 5/2014 | Rapoport |
| 2014/0139216 | A1 | 5/2014 | Rapoport |
| 2014/0142914 | A1 | 5/2014 | Rapoport |
| 2014/0152302 | A1 | 6/2014 | Rapoport et al. |
| 2014/0152310 | A1 | 6/2014 | Rapoport |
| 2014/0158062 | A1 | 6/2014 | Rapoport et al. |
| 2014/0230850 | A1 | 8/2014 | Rapoport |
| 2014/0257081 | A1 | 9/2014 | Rapoport |
| 2014/0266203 | A1 | 9/2014 | Rapoport |
| 2014/0300358 | A1 | 10/2014 | Rapoport |
| 2014/0378821 | A1 | 12/2014 | Rapoport et al. |
| 2014/0378825 | A1 | 12/2014 | Rapoport et al. |
| 2015/0065788 | A1 | 3/2015 | Rapoport |

OTHER PUBLICATIONS

Aspect Imaging Ltd., "Cage in an MRD with a Fastening/Attenuating System", co-pending U.S. Appl. No. 14/527,950, filed Oct. 30, 2014.

Rapoport, Uri, "RF Shielding Conduit in an MRI Closure Assembly", co-pending U.S. Appl. No. 14/574,785, filed Dec. 18, 2014.

Aspect Imaging Ltd., "System and Method for Generating Invasively Hyperpolarized Images", co-pending U.S. Appl. No. 14/556,654, filed Dec. 1, 2014.

Aspect Imaging Ltd., "MRI with Magnet Assembly Adapted for Convenient Scanning of Laboratory Animals with Automated RF Tuning Unit", co-pending U.S. Appl. No. 14/581,266, filed Dec. 23, 2014.

Aspect Imaging Ltd., "Chamber for Housing Animals During Anaesthetic Procedures", co-pending U.S. Appl. No. 14/537,266, filed Nov. 10, 2014.

Aspect Imaging Ltd., "RF Automated Tuning System Used in a Magnetic Resonance Device and Methods Thereof", co-pending U.S. Appl. No. 14/588,741, filed Jan. 2, 2015.

Aspect Imaging Ltd., "Means for Operating an MRI Device Within a RF-Magnetic Environment", co-pending U.S. Appl. No. 14/596,320, filed Jan. 14, 2015.

Aspect Imaging Ltd., "Means and Method for Operating an MRI Device Within a RF-Magnetic Environment", co-pending U.S. Appl. No. 14/596,329, filed Jan. 14, 2015.

Aspect Imaging Ltd., "CT/MRI Integrated System for the Diagnosis of Acute Strokes and Methods Thereof", co-pending U.S. Appl. No. 14/598,517, filed Jan. 16, 2015.

Aspect Imaging Ltd., "Method for Providing High Resolution, High Contrast Fused MRI Images", co-pending U.S. Appl. No. 13/877,553, filed Apr. 3, 2013.

Aspect Imaging Ltd., "Foamed Patient Transport Incubator", co-pending U.S. Appl. No. 14/531,289, filed Nov. 3, 2014.

Aspect Imaging Ltd., "Mechanical Clutch for MRI", co-pending U.S. Appl. No. 14/611,379, filed Feb. 2, 2015.

Aspect Imaging Ltd., "Incubator Deployable Multi-Functional Panel", co-pending U.S. Appl. No. 14/619,557, filed Feb. 11, 2015.

Aspect Imaging Ltd., "MRI Thermo-Isolating Jacket", co-pending U.S. Appl. No. 14/623,039, filed Feb. 16, 2015.

Aspect Imaging Ltd., "MRI RF Shielding Jacket", co-pending U.S. Appl. No. 14/623,051, filed Feb. 16, 2015.

Aspect Imaging Ltd., "Capsule for a Pneumatic Sample Feedway", co-pending U.S. Appl. No. 14/626,391, filed Feb. 19, 2015.

Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.

Aspect Imaging Ltd., "Temperature-Controlled Exchangeable NMR Probe Cassette and Methods Thereof", co-pending U.S. Appl. No. 14/504,890, filed Oct. 2, 2014.

Aspect Imaging Ltd., "NMR Extractable Probe Cassette Means and Methods Thereof", co-pending U.S. Appl. No. 14/504,907, filed Oct. 2, 2014.

Aspect Imaging Ltd., "Method for Manipulating the MRI's Protocol of Pulse Sequences", co-pending U.S. Appl. No. 14/070,695, filed Nov. 4, 2013.

* cited by examiner

CHAMBER FOR HOUSING ANIMALS DURING ANAESTHETIC PROCEDURES

FIELD OF THE INVENTION

The present invention generally pertains to flat sealing mechanism for glovebox-like chambers and more specifically, sealing mechanisms and methods for animal treating in high pressure anaesthetic chambers.

BACKGROUND OF THE INVENTION

Encapsulated boxes (usually called gloveboxes), routinely utilized e.g., in sterile medicine activities, pharmaceutics preparations, food analysis, and hazards and radioactive contaminatable uses are known in the art. In U.S. Pat. No. 4,251,123 to Brackenbush, a flap or door like solution is offered for use with a radioactive safe glove box. The flaps are however, heavy and gravity sensitive, resilient and stiff, rendering the openings leaky with respect to gases and biohazards. U.S. Pat. Nos. 2,528,332; 2,436,291; 2,803,370; 3,086,674; 4,331,254 and 5,104,206 disclose a few embodiments of a glove-less glovebox, having one or more operator hand access port (OHAP) sealed by either (i) one flexible membrane having a star-like (not a port or aperture-crossing-) centralized aperture into which the hand of the operator is inserted, or (ii) a multilayered stack composed of a few flexible membranes, each of which has a star-like centralized aperture into which the hand of the operator is inserted. The aforementioned apertures are slightly disoriented (e.g., rotated) with respect to each another or slightly dislocated (e.g., decentralized) with respect to each other. The aforesaid embodiments are suitable solely for non-pressurized gloveboxes. U.S. Pat. No. 3,450,450 presents a pressure resistant seal which comprises a means defining an aperture and a plurality of closures members of flexible sheet material, attached in a bulky manner side-by-side to the periphery of the aperture, such that the stacked sheets are set perpendicular to the aperture cross section and a thick sealing. Such an arrangement is not suitable for certain high-pressure gloveboxes, especially animal-treating gloveboxes (e.g., anaesthetic chambers).

It is clear from the above that there is a long felt and unmet need for means and methods to enable a human operator to manipulate with dexterity small mammals in a ventilation hood or anaesthetic chamber without gas escaping from the aforementioned chamber into the surrounding environment.

SUMMARY OF THE INVENTION

An aspect of the invention is to provide a chamber (a glovebox or the like) having at least one operator hand access port (OHAP). The OHPA comprises, inter alia, (i) a port aperture located within the chamber wall; and (ii) at least two flexible non-resilient lightweight sealing gas-tight flaps (SFs). The SFs are disposed within substantially the same plane of the port aperture in an overlapping manner, entirely enclosing the port aperture. Each of the SFs is defined by a port aperture edge and chamber edges. In a novel and inventive manner, the chamber edges are preferably anchored to the chamber wall along more than half of the perimeter of the flap, at a distance from the center of the port greater than the radius of the port and beyond its perimeter. Similarly, the port aperture edge of each flap is stretched across (and possibly beyond) an entire chord of the port aperture. Hence, such the stretched port apertures edges define an interior access zone, disposed within the same plane of the port aperture, characterized solely by the port aperture edges of the SFs.

Another aspect of the invention is to provide the chamber as defined above, wherein each of the SFs is a sheet-like member defined in a shape selected from a group consisting, inter alia, of truncated circle; polygon, especially a polygon of a rectangular shape and a combination thereof.

Another aspect of the invention is to provide the chamber as defined in any of the above, wherein the OHAP comprises a plurality of M SFs, M is an integer ranging from 2 to 6; alternatively from 4 to 10; alternatively from 6 to 18; or alternatively from 10 to 60.

Another aspect of the invention is to provide the chamber as defined in any of the above, wherein at least a portion of the SFs is non-rigid membrane, anchored to the chamber's wall by means of a gasket assembly. The gasket assembly is characterized by a clamping mechanism, such as press-clamps mechanism, nuts-based or screws-based clamping mechanism, weld or otherwise glued clamping mechanism etc.

Another aspect of the invention is to provide the chamber as defined in any of the above, wherein the chamber is at least partially transparent. The chamber is possibly made in some of its parts of polymers, such as plastic, polyethylene, polypropylene, polycarbonate, polymethyl methacrylates, cardboards, metals, glass, and combination thereof.

Another aspect of the invention is to provide the chamber as defined in any of the above, wherein the chamber comprises a plurality of N operator hand access ports; N is integer >1, e.g., N=1; N≥2; N=4, 7, 120 etc.

Another aspect of the invention is to provide the chamber as defined in any of the above, wherein the chamber comprises at least one (optionally valved-) inlet and/or outlet to provide a fluid to and/or from the chamber, such that the pressure and/or volume of the fluid within the chamber is different (i.e., lower or higher) from outside the chamber; and further wherein SFs provide fluid-tight sealing across the port aperture during operation of the chamber and manipulations therein.

Another aspect of the invention is to provide the chamber as defined in any of the above, wherein the SFs fluid-tight sealing mechanism is adapted to set under a positive gas pressure.

Another aspect of the invention is to provide the chamber as defined in any of the above, wherein the chamber adapted by means of size and shape for housing animals, especially small mammals, such as laboratory animals, e.g., vertebrates, invertebrates frogs, guinea pigs, hamsters, gerbils, mice, rats, rabbits, cats, canines etc. The term 'animal' thus refers hereinafter to any laboratory animals, single or plural. The term also refers to other animals, such as fish and aquatic creatures, haplorrhines, primates and humans.

Another aspect of the invention is to provide the chamber as defined in any of the above, wherein the chamber is adapted, e.g., by means of size and shape, for treating anaesthetized animals. Hence, the chamber is characterized, inter alia, by (i) a mechanism adapted to provide a positive anaesthetizing gas pressure within at least a portion of the chamber's volume; and (ii) by a SFs fluid-tight sealing mechanism, which is adapted to set under the gas pressure.

Another aspect of the invention is to provide the chamber as defined in any of the above, wherein at least one or each of the SFs comprises at least one substantially horizontal section (H) and at least one substantially vertical (V) section. The sections are set at predetermined colliding orientations to each other.

Another aspect of the invention is to provide the chamber as defined in any of the above, wherein at least one access port is located within the chamber on a location selected from a group consisting of the side of the chamber; the bottom of the chamber; the roof of the chamber and a combination thereof.

Another aspect of the invention is to provide the chamber as defined in any of the above, wherein the SFs are sheet-like (two dimensional) and/or bulky (three dimensional) members.

Another aspect of the invention is to provide the chamber as defined in any of the above, wherein the SFs are made of disposable materials; alternatively or additionally, the SFs are disposable items. Similarly, the chamber or parts thereof is made of disposable materials; alternatively or additionally, the chamber or parts thereof is a disposable item.

Another aspect of the invention is to provide the chamber as defined in any of the above, wherein the SFs are at least partially made of materials, selected in a non-limiting manner from the group consisting of rubber, latex, polyamides, nylons, or elastomers and a combination thereof.

Another aspect of the invention is to provide the chamber as defined in any of the above, wherein the OHAP is adapted to be sealable against a gas. The gas is selected in a non-limiting manner from the group consisting of oxygen, nitrogen, air, steam, any purging gas, isoflourane, methoxyflurane, halofluorane, desfluorane, sevofluorane, nitrous oxide, ether and any combination and mixtures thereof.

Another aspect of the invention is to provide the chamber as defined in any of the above, wherein the chamber is provided with a hermetically sealed communication mechanism, communicating the interior volume of the chamber with (i) an imaging device, such as an NMR, MRI, or CT, (ii) medically treating device, such as De Vinci™ medical robot, laporascope or gastroscope, trocar, intravenous fluids irrigating mechanism etc., such that the animal is inserted and withdrawn, manipulated, dislocated, oriented, approached near, or otherwise introduced from and to the imaging and treating device without escape of gas from the interior of the chamber.

Another aspect of the invention is to provide the chamber as defined in any of the above, wherein the chamber is adapted, e.g., by means of size and shape, to at least reversibly accommodate at least one animal. The chamber comprises at least one mechanism selected from a group consisting of a drop system mechanism for administration of a fluid, especially an anesthetic material, to the animal; an anesthetic machine for administration of anaesthesia to the animal; fluid's feeding mechanism for administration of drug, food or drinking to the animal; optical magnifying means (OMM) for viewing the animals; apertures for immobilizing, medically treating and/or imaging the animal; and a combination thereof.

Another aspect of the invention is to provide the chamber as defined in any of the above, wherein OMM is selected from a group consisting of magnifying lens, magnifying mirrors, binoculars and microscopes. The OMM is possibly embedded within the walls and/or roof of the chamber.

Another aspect of the invention is to provide the chamber as defined in any of the above, wherein the chamber is dust proof, and/or biohazard proof.

Another aspect of the invention is to provide a method for providing a fluid-tight sealed chamber. This method comprises steps of providing at least one operator hand access port as defined in any of the above; providing the port with a port aperture located within the chamber wall and at least two flexible non-resilient lightweight sealing gas-tight SFs; disposing the SFs within substantially the same plane of the port aperture in an overlapping manner, entirely enclosing the port aperture; defining each of the SFs by a port aperture edge and chamber edges. This method is characterized by step of anchoring the chamber edges to the chamber wall along more than half of the perimeter of the flap, at a distance from the center of the port greater than the radius of the port and beyond its perimeter. This method is further characterized by step of stretching the port aperture edge of each flap across (and possibly beyond-) an entire chord of the port aperture, and thus defining the stretched port apertures edges with an interior access zone, disposed within the same plane of the port aperture, characterized solely by the port aperture edges of the SFs.

Still another aspect of the invention is to provide a method for manipulating, medically treating or imaging animals during anaesthetic procedures without exposure of the surroundings to escaping gases. The method comprises steps of obtaining a chamber as defined in any of the above; placing an animal (one or more) in the chamber; anaesthetizing the animal with an anaesthetizing gas; manipulating, medically treating or imaging the animal via the access ports such that substantially no gases escape from the chamber.

Another aspect of the invention is to provide an integrated imaging system for imagine or otherwise treat anesthetized animals, the system comprising (a) a chamber set in a shape and dimensions to at least temporarily accommodating an animal to be anesthetized, imagined or otherwise treated. The chamber is potentially provided in a manner as defined in any of the above; (b) an imaging treating and/or device useful for imaging or otherwise treating the animal; and (c) bridging mechanism in connection with the chamber and the device.

BRIEF DESCRIPTION OF THE DRAWINGS

This invention will now be described in more detail, by presenting examples, with references to the accompanying drawings.

DETAILED DESCRIPTION THE PREFERRED EMBODIMENTS

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a high pressure chamber, e.g., for housing small mammals during anesthetic The sealed chamber disclosed in the present invention is sealable against all gases used in the chamber, including purging gases, anaesthetic gases and water vapour or nay other vapour. The gases may be used for maintaining or controlling the body temperature of the small mammal. It is further acknowledged that the small mammal may be administered the anaesthetic via intubation, convection or any other means known in the art.

Several core aspects of the present invention are represented in the Table 1 below, in comparison with prior art U.S. Pat. No. 4,251,123.

TABLE 1

The differences between the present invention and the seal disclosed in prior art

| | Present invention | U.S. Pat. No. 4,251,123 |
|---|---|---|
| Biohazard sealable | 100% | 0% |
| Gas proof | 100% | 20% |
| Dust and flowing-matter proof | 100% | 20% |
| Radiation proof | 0% | 100% |
| Gravity sensitive | 0% | 100% |
| Shroud-like opening | 100% | 20% |
| Flexibility | 100% | 40% |

TABLE 1-continued

The differences between the present invention and the seal disclosed in prior art

| | Present invention | U.S. Pat. No. 4,251,123 |
|---|---|---|
| Resiliency | 0% | 100% |
| Thickness | 2D Thin arrangement | 3D Thick arrangement |

Figure 1:
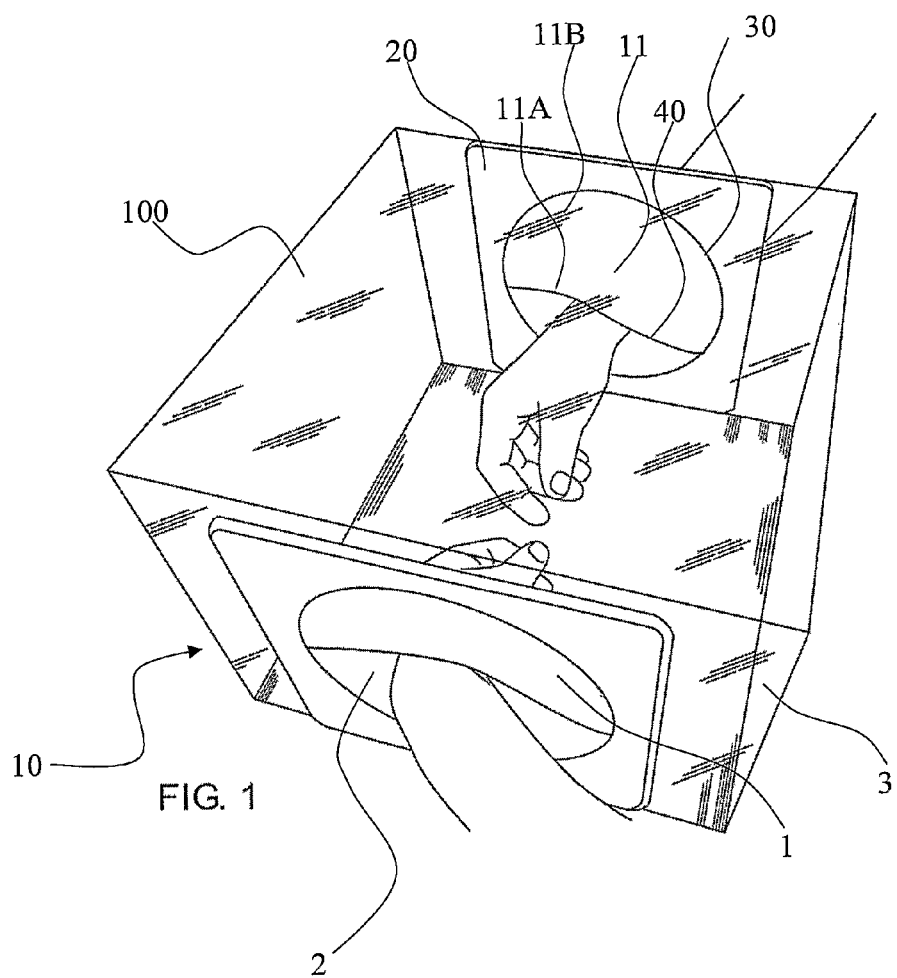
FIG. 1 is a schematic representation (perspective view) of a chamber according to one embodiment of the invention for housing small mammals during anesthetic procedures having two oppositely located OHAPs, sealable against escaping gas when two operator hand enters the chamber and the chamber is under positive gas pressure.

Reference is now made to FIG. 1 which is a schematic representation (perspective view) of a chamber according to one embodiment of the invention. This chamber is provided useful for e.g., housing small mammals during anesthetic procedures. The chamber (100) has two oppositely located OHAPs (10, 11), sealable against escaping gas when two operator hand enters the chamber and the chamber is under positive gas pressure. The port, comprises a port aperture located within the chamber wall (3); and at least two flexible non-resilient lightweight sealing gas-tight flaps (SFs: 1, 2), disposed within the same plane of the port aperture in an overlapping manner, entirely enclosing the port aperture. Each of SFs 1 and 2 is defined by a port aperture edge (e.g., 11A) and chamber edges (e.g. 11B). The chamber edges are anchored to the chamber wall along more than half of the perimeter of the flap, at a distance from the center of the port greater than the radius of the port and beyond its perimeter. The SFs are anchored in FIG. 1 by means of clamp 20. The port aperture edge of each flap is stretched across an entire chord of the port aperture; such that the stretched port apertures edges define an interior access zone 40, disposed within the same plane of the port aperture 30, characterized solely by the port aperture edges of the SFs.

Figure 2:
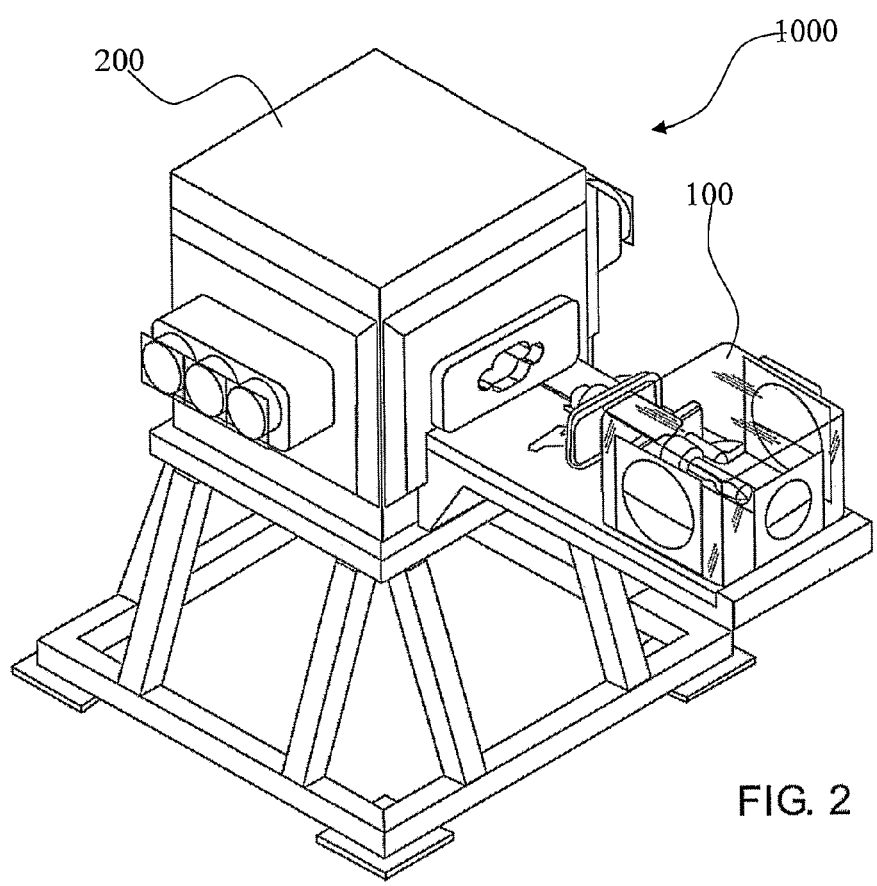
FIG. 2 is a schematic representation (perspective view) of a chamber according to another embodiment of the invention, set aside an MRI imaging device as an integrated (connectable) anesthetizing, treating and imaging system.

Reference is now made to FIG. 2 which is a schematic representation (perspective view) of a chamber 100 according to another embodiment of the invention, alongside an MRI imaging device 200 as an integrated (connectable) anesthetizing, treating and imaging system 1000.

In some embodiments of the invention, a bridging mechanism and/or a conveying mechanism is provided for conveying an animal between the chamber and the MRI.

Figure 3A:
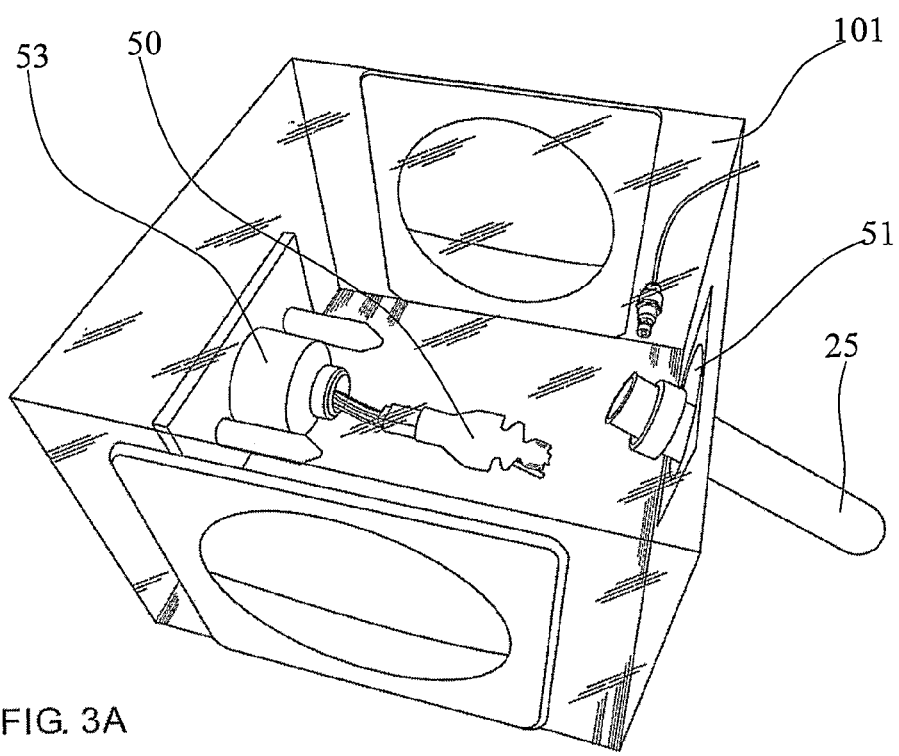
FIG. 3a is a schematic representation (perspective view) of a chamber according to another embodiment of the invention, the chamber accommodates means for anesthetizing, treating and imaging animals.

Reference is now made to FIG. 3a which is a schematic representation (perspective view) of a chamber 101 according to another embodiment of the invention; the chamber accommodates means for anesthetizing, treating and imaging animals: support (e.g., bed or stretcher) 50, equipment inlet 51 and encapsulating tube 52, bridging mechanism 53 in connection with the imaging device 200 (not shown) etc.

Figure 3B:
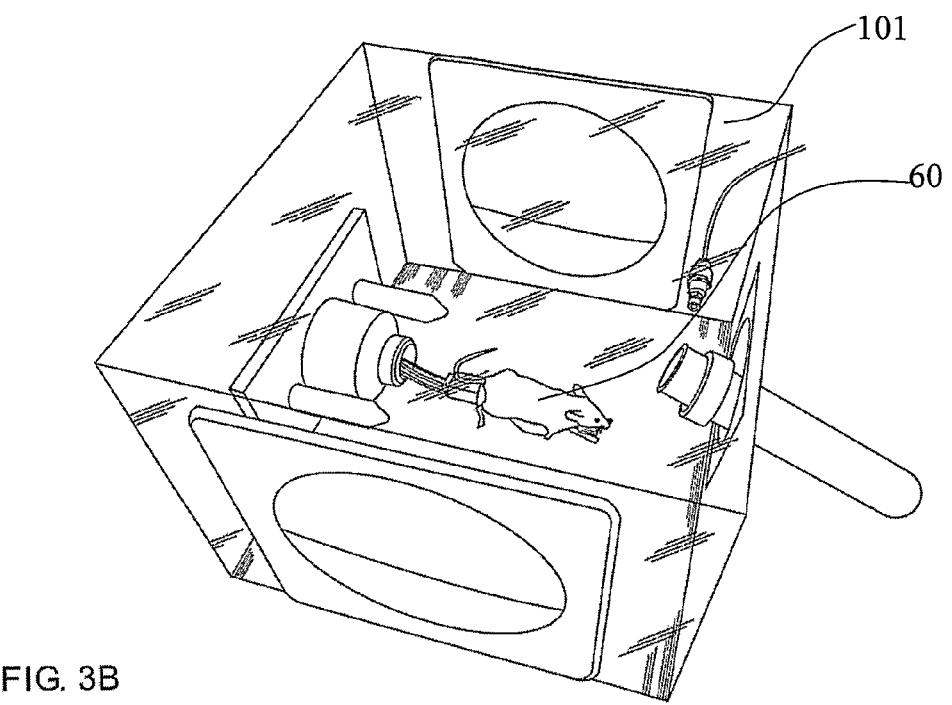
FIG. 3b is a schematic representation (perspective view) of a chamber according to another embodiment of the invention, the chamber accommodates a support for laying the anesthetized animal before imaging.

Reference is now made to FIG. 3b which is a schematic representation (perspective view) of a chamber 101 according to an embodiment of the invention; the chamber accommodates a support for laying the anesthetized animal 60 before imaging.

Figure 3C:
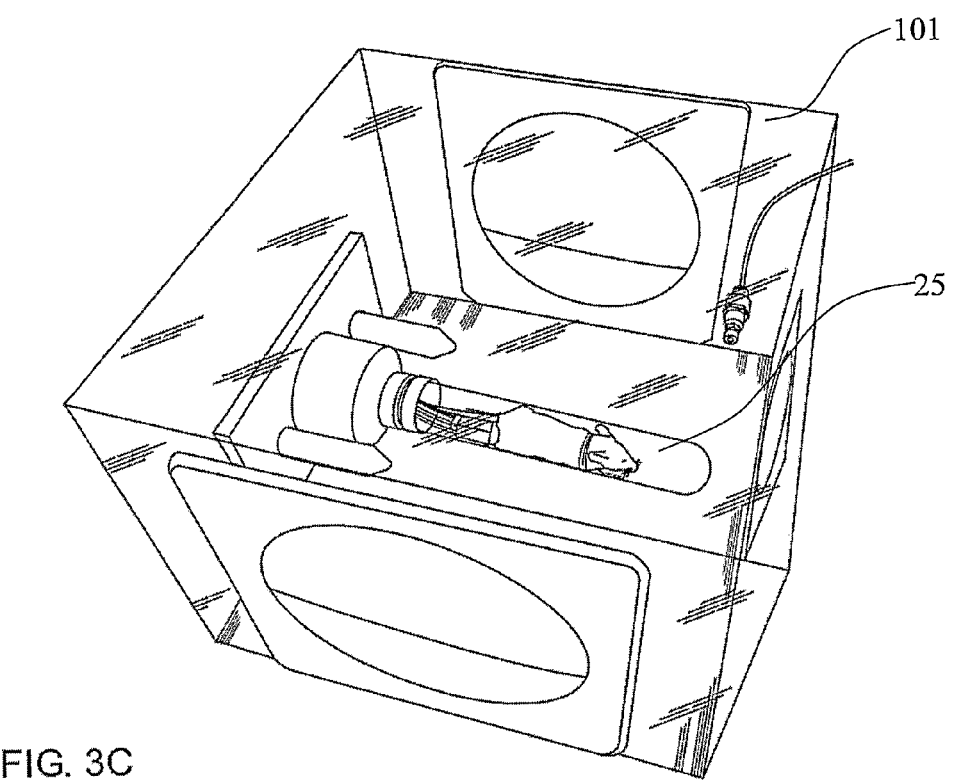
FIG. 3c is a schematic representation (perspective view) of a chamber according to another embodiment of the invention, the chamber accommodates an encapsulated container in which the support for laying the anesthetized animal before imaging is reversibly provided.

Reference is now made to FIG. 3c which is a schematic representation (perspective view) of a chamber according to the said embodiment of the invention, the chamber accommodates an encapsulated container 25 in which support 50 for laying the anesthetized animal 60 before imaging is reversibly provided.

Figure 4:
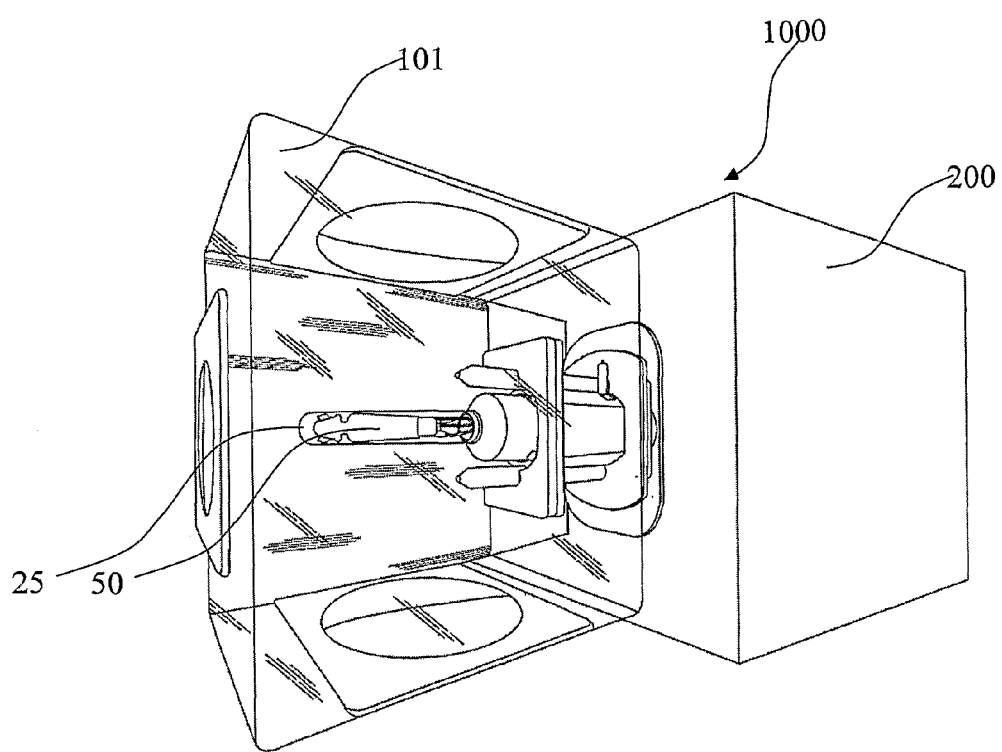
FIG. 4 is a front and top view of an integrated anesthetizing, treating and imaging system according to another embodiment of the invention; in an initial step, the chamber accommodates an encapsulated container in which the support for laying the anesthetized animal before imaging is reversibly provided.

Reference is now made to FIG. 4 which is a front and top view of an integrated anesthetizing, treating and imaging system 1000 according to the said embodiment of the invention. In an initial step, chamber 101 accommodates an encapsulated container 25 in which the support 50 for laying the anesthetized animal 60 (not shown) before imaging is applied within the imaging device 200.

Figure 5:
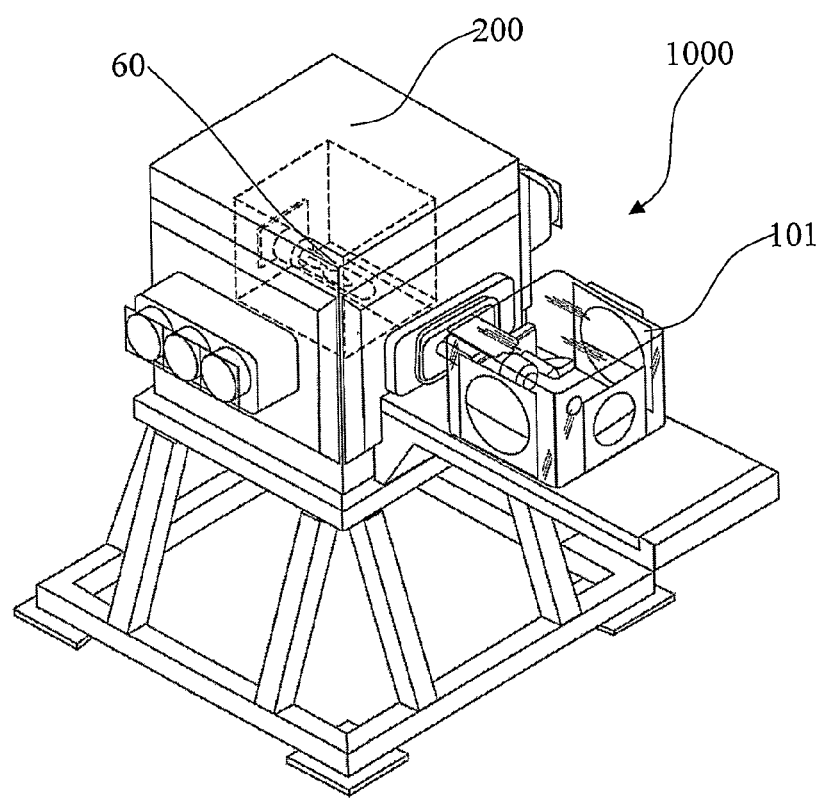
FIG. 5 is a schematic representation (perspective view) of an integrated anesthetizing, treating and imaging system 1000 according the said embodiment of the invention; in a following step, the encapsulated container 60 in which the support for laying the anesthetized animal is introduced within the imaging device 200 via the bridging mechanism. Container 101 is temporarily free of animals in this step.
Figure 6A:
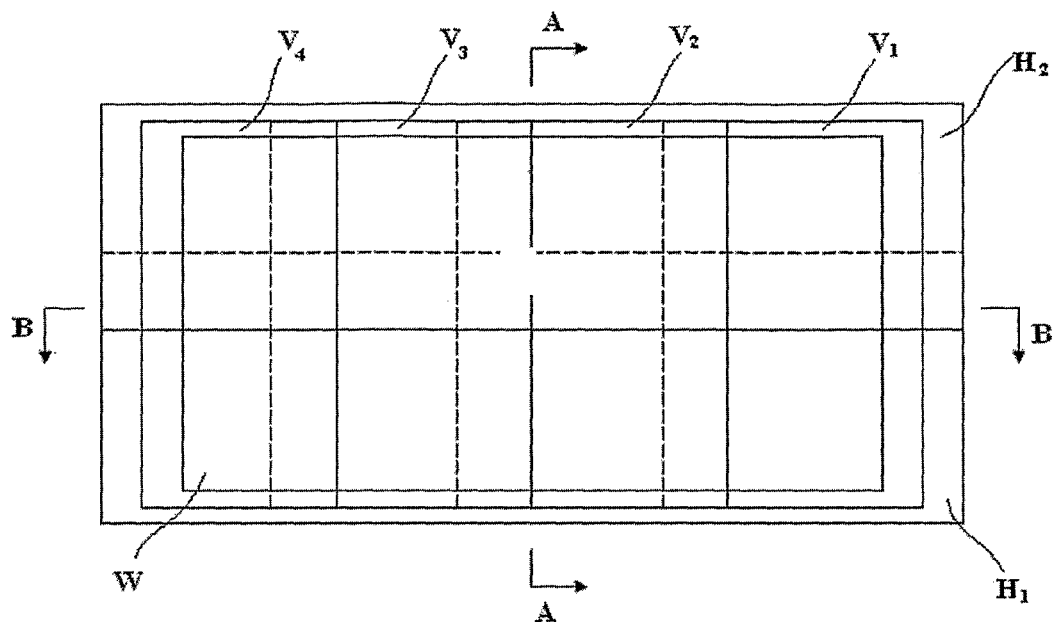
FIG. 6a is a schematic representation (top view) of SFs arrangement having H type and V type flaps orientations according to another embodiment of the invention.
Figure 6B:
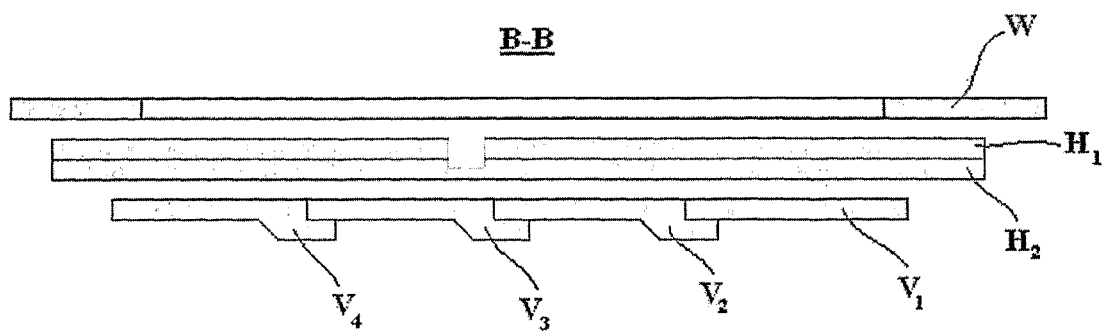
FIG. 6b is a schematic representation (1$^{st}$ side view) of the same.
Figure 6C:
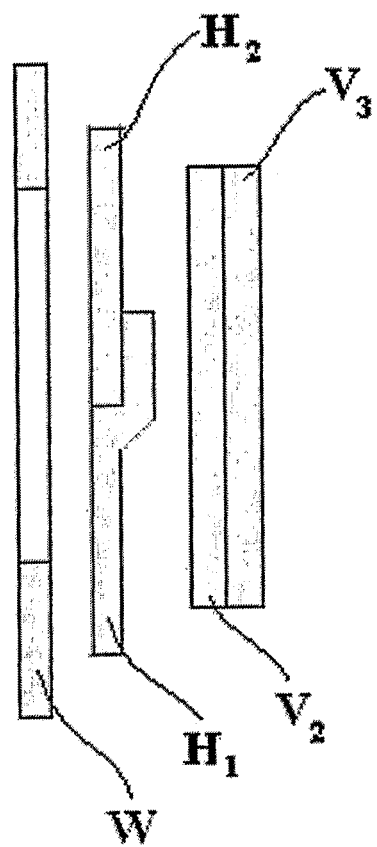
FIG. 6c is a schematic representation (2$^{nd}$ side view) of the same.

System 1000 is thus an example of an integrated imaging system for imagine or otherwise treat anesthetized animals, the system comprising (a) a chamber set in a shape and dimensions to at least temporarily accommodating an animal to be anesthetized, imagined or otherwise treated. The chamber is potentially provided in a manner as defined in any of the above; (b) an imaging treating and/or device useful for imaging or otherwise treating the animal; and (c) bridging mechanism in connection with the chamber and the device. Reference is now made to FIG. 5 which is a schematic representation (perspective view) of an integrated anesthetizing, treating and imaging system according to another embodiment of the invention; in a following step, the encapsulated container in which the support for laying the anesthetized animal is introduced within the imaging device via a bridging mechanism; Reference is now made to FIG. 6a which is a schematic representation (top view) of SFs arrangement having H type and V type flaps orientations according to another embodiment of the invention;

FIG. 6b is a schematic representation ($1^{st}$ side view) of the same; FIG. 6c is a schematic representation ($2^{nd}$ side view) of the same. In an illustrative manner, a cutout panel or window W is provided in the wall of the chamber. A horizontal SF H1 is stretched and fixed across the cutout, in such a way as to leave an uncovered gap in the cutout of about one third. A horizontal SF H2 is stretched across the membrane in such a way as to overlap the bottom two thirds portion of H1 and complete the coverage of H2. Thus the panel or window W is now covered from the outside, yet can be penetrated by an object, negotiating it's access way or path between layers formed by H1 and H2. The aforementioned H1 and H2 SFs taken together are designated herein as the H section. A vertical (V) section is also formed: Vertical apertures V1, V2, V3 and V4 are overlappingly stretched along the panel in the following manner: V1 is stretched vertically down the right side of the panel, covering about one quarter of the panel. V2 is stretched vertically down the right side of the panel but somewhat leftwards from the side, overlaid on V1 and overlapping V1 by about one third of it's width. V3 is stretched vertically down the right side of the panel over V2 but somewhat leftwards over the V2s right margin, overlaid on V2, overlapping V2 by about one third. V4 is stretched vertically down the right side of the panel over V3 but somewhat leftwards over the V3 right margin, overlaid on V3, overlapping V3 by about one third. The panel is now completely covered by elastic gas proof SFs since the H section and the V section separately and together completely cover the cutput panel in the wall of the chamber and render it gas proof and leak proof. Moreover, and this is a core aspect of the invention, a hand or arm can easily penetrate the opening formed by the panel and into the chamber by simply negotiating it's access way through a passage formed the overlaid layers of stretched elastic membrane material. In the arrangement described above, it is clear that there are three locations along the panel where an arm or hand can most easily penetrate the chamber and manipulate within it wherein over-pressured or positive pressure gas does not escape.

Figure 7:
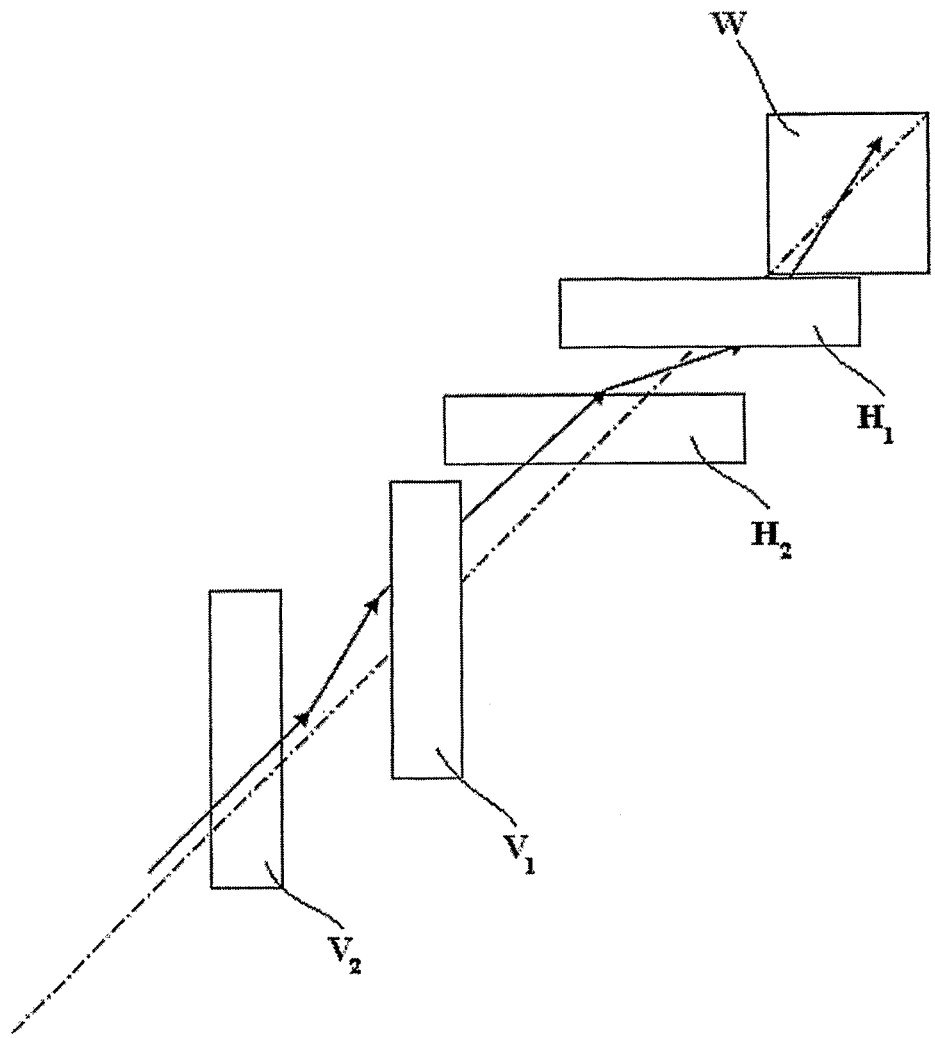
FIG. 7 is a schematic representation (cross section) of an interior access zone in an SFs arrangement having H type and V type flaps orientations according to another embodiment of the invention.
Figure 8:
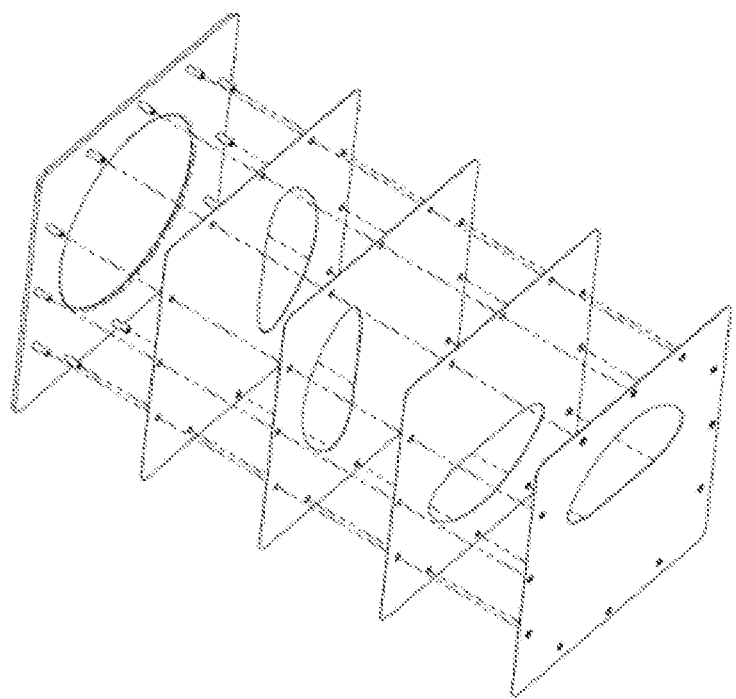
FIG. 8 is a schematic representation (perspective view) of an SFs arrangement having H type and V type rotetably distorted flaps orientations according to another embodiment of the invention, here the flaps is having textures, apertures, openings etc)

Reference is now made to FIG. 7 which is a schematic representation (cross section) of an interior access zone in an SFs arrangement having H type and V type flaps orientations according to another embodiment of the invention;

Reference is now made to FIG. 8 which is a schematic representation (perspective view) of an SFs arrangement having H type and V type rotetably distorted flaps orientations according to another embodiment of the invention, here the flaps is having textures, apertures, openings etc).

Figure 9:
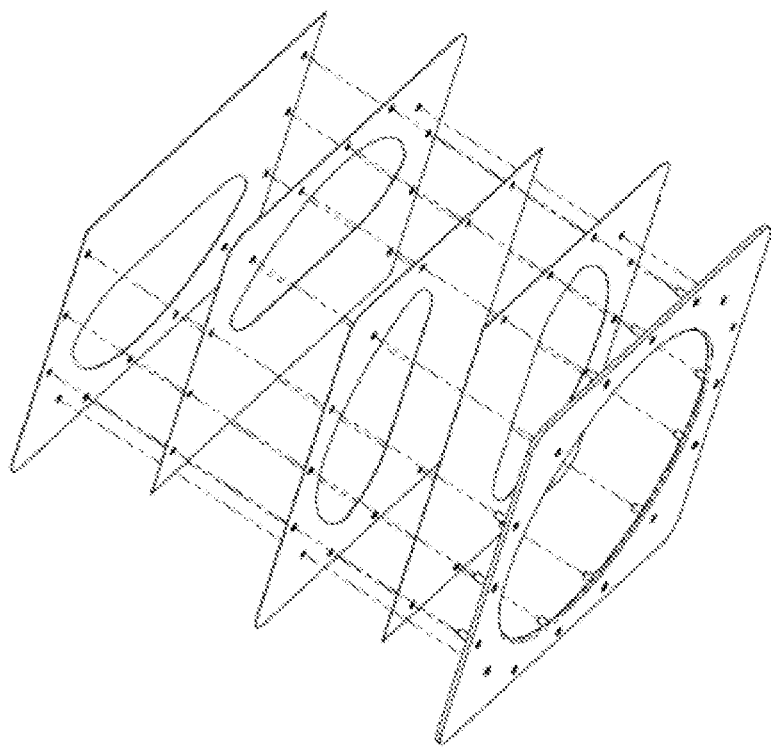
FIG. 9 is a schematic representation (perspective view) of an SFs arrangement having H type and V type dislocated flaps orientations (dislocation along the X-Y main plane of the aperture) according to another embodiment of the invention, here again the flaps is having textures, apertures, openings etc)

Reference is now made to FIG. 9 which is a schematic representation (perspective view) of an SFs arrangement having H type and V type dislocated flaps orientations (dislocation along the X-Y main plane of the aperture) according to another embodiment of the invention, here again the flaps is having textures, apertures, openings etc).

Figure 10:
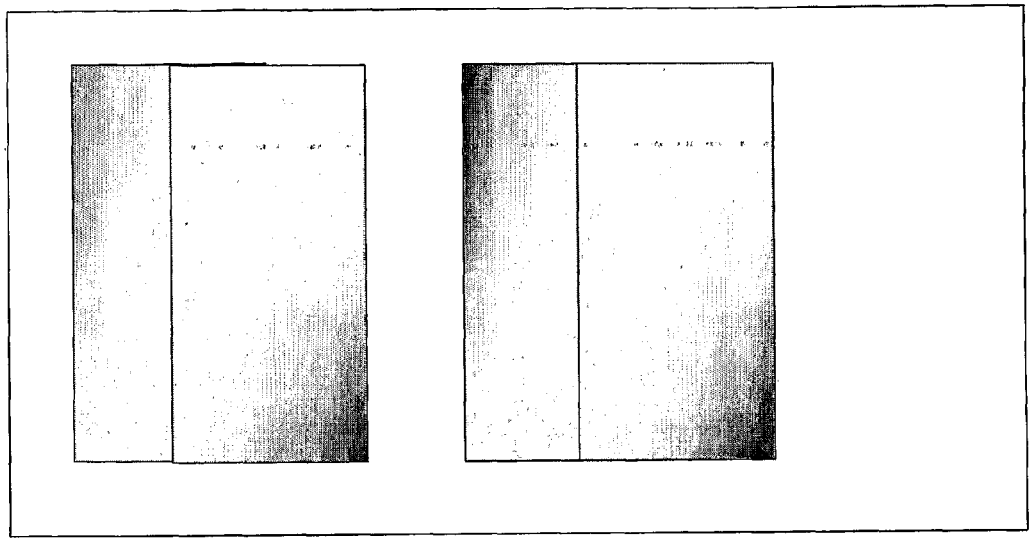
FIG. 10 is a schematic representation (top view) of an SFs parallel arrangement according to another embodiment of the invention; and, FIG. 11 is a schematic representation (top view) of an SFs twisted arrangement according to another embodiment of the invention.
Figure 11:
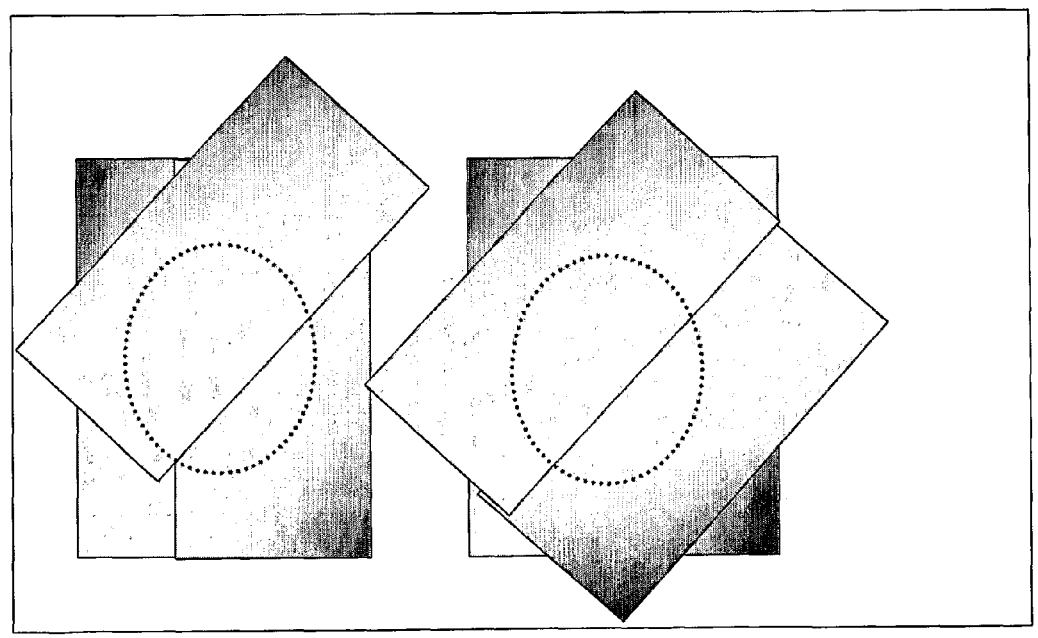

Reference is now made to FIG. 10 which is a' schematic representation (top view) of SFs parallel arrangement according to another embodiment of the invention; and, Reference is now made to FIG. 11 which is a schematic representation (top view) of SFs twisted arrangement according to another embodiment of the invention.

The invention claimed is:

1. A closed chamber having a positive pressure of gas there inside, the chamber comprising at least one gas-tight operator hand access port configured to enable an operator to access and manipulate subjects located within said chamber without gas escaping from the chamber into the surrounding environment;

wherein said at least one hand access port comprises:
a port aperture located within a chamber wall;
at least two first partially overlapping flexible and elastic lightweight sealing gas-tight flaps (SFs) disposed within the same plane of said port aperture, forming at least one first overlapping area, said at least two first SFs entirely enclosing said port aperture, and
at least two second partially overlapping SFs overlaid on said first SFs in contact therewith, forming at least one second overlapping area, said at least one first and at least one second overlapping areas are orthogonal to each other;
wherein each of said SFs is defined by a port aperture edge and chamber edges, said chamber edges are anchored to said chamber wall and said port aperture edge is a straight line stretched across an entire chord of said port aperture,
wherein said at least one first and said at least one second overlapping areas are formed between respective aperture edges of said at least two first and at least two second partially overlapping SFs such that said port aperture edges define at least two interior access zones, and wherein access into said chamber through said at least two interior access zones is provided by at least one change of direction of said operator's hand.

2. The chamber of claim 1, wherein each of said SFs is a sheet-like member defined in a shape selected from a group consisting of truncated circle; polygon; and any combination thereof.

3. The chamber of claim 1, comprising SFs in a number ranging from a group consisting of from 2 to 6; from 4 to 10; from 6 to 18; and from 10 to 60.

4. The chamber of claim 1, comprising a plurality of N operator hand access ports; N is integer greater than 1.

5. The chamber of claim 1, wherein said chamber comprising at least one inlet and/or outlet to provide a fluid to and/or from said chamber, such that the pressure and/or volume of said fluid within said chamber is different from outside said chamber; further wherein SFs provide fluid-tight sealing across said port aperture during operation of said chamber and manipulations therein.

6. The chamber of claim 1, adapted by means of size and shape for housing animals.

7. The chamber of claim 1, adapted by means of size and shape for treating anaesthetized animals, said chamber is characterized by a mechanism to provide a positive anaesthetizing gas pressure within said at least a portion of said chamber's volume.

8. The chamber of claim 1, wherein said at least one access port is located on a location selected from a group consisting of the side of said chamber; the bottom of said chamber; the roof of said chamber and a combination thereof.

9. The chamber of claim 1, wherein said chamber is provided with a hermetically sealed communication means to a small mammal imaging device, such that said small mammal may be inserted and withdrawn from said imaging device without escape of gas from the interior of said chamber.

10. The chamber of claim 1, wherein said chamber is adapted by means of size and shape to at least reversibly accommodate at least one animal, said chamber comprising at least one mechanism selected from a group consisting of a drop system mechanism for administration of a fluid to said animal; an anesthetic machine for administration of anaesthesia to said animal; fluid feeding mechanism for administration of at least one drug to said animal; fluid feeding mechanism for administration of at least one food to said animal; fluid feeding mechanism for administration at least one drink to said animal; optical magnifying means (OMM) for viewing said animals; apertures for immobilizing, medically treating and/or imaging said animal; and any combination thereof.

11. A method for manipulating, medically treating or imaging animal during anaesthetic procedures without exposure to escaping gases, wherein said method comprising:
   a) providing a chamber according to claim 1;
   b) placing said animal in said chamber;
   c) anaesthetizing said animal with an anaesthetizing gas; and
   d) manipulating said animal via said at least one hand access port such that substantially no gases escape from said chamber.

12. An integrated imaging system for imaging or otherwise treating anesthetized animals, said system comprising (a) a chamber according to claim 1 set in a shape and dimension to at least temporarily accommodating an animal to be anesthetized, imaged or otherwise treated, (b) an imaging treating and/or device useful for imaging or otherwise treating said animal; and (c) a bridging mechanism in connection with said chamber and said device.

* * * * *